US009880187B2

(12) United States Patent
Shibuya et al.

(10) Patent No.: US 9,880,187 B2
(45) Date of Patent: Jan. 30, 2018

(54) MOTION ANALYSIS METHOD AND MOTION ANALYSIS APPARATUS (71) Applicant: SEIKO EPSON CORPORATION, Tokyo (JP)

(72) Inventors: Kazuhiro Shibuya, Shiojiri (JP); Masafumi Sato, Hara-mura (JP); Kazuo Nomura, Shiojiri (JP); Kenya Kodaira, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 543 days.

(21) Appl. No.: 14/509,589

(22) Filed: Oct. 8, 2014

(65) Prior Publication Data
US 2015/0106050 A1 Apr. 16, 2015

(30) Foreign Application Priority Data
Oct. 11, 2013 (JP) ................................. 2013-213476

(51) Int. Cl.
G06F 19/00 (2011.01)
G01P 3/00 (2006.01)
G09B 19/00 (2006.01)

(52) U.S. Cl.
CPC .............. *G01P 3/00* (2013.01); *G09B 19/003* (2013.01); *G09B 19/0038* (2013.01); *G06F 19/3481* (2013.01)

(58) Field of Classification Search
CPC .... C07C 51/252; C07C 57/04; G06Q 30/0601
USPC ................. 702/142, 150, 182–185
See application file for complete search history.

(56) References Cited

U.S. PATENT DOCUMENTS

| 8,109,816 | B1 | 2/2012 | Grober |
| 2009/0247312 | A1 | 10/2009 | Sato et al. |
| 2011/0299729 | A1 | 12/2011 | Dawe et al. |
| 2014/0111625 | A1 | 4/2014 | Dawe et al. |
| 2014/0195184 | A1* | 7/2014 | Maeda ................. G01D 18/006 702/85 |

FOREIGN PATENT DOCUMENTS

| JP | A-11-169499 | 6/1999 |
| JP | A-2004-024488 | 1/2004 |
| JP | A-2008-073210 | 4/2008 |
| JP | A-2009-125507 | 6/2009 |
| JP | A-2009-240677 | 10/2009 |
| JP | A-2010-011926 | 1/2010 |
| JP | A-2010-068947 | 4/2010 |
| JP | A-2010-110382 | 5/2010 |
| JP | A-2013-088875 | 5/2013 |
| JP | A-2013-521077 | 6/2013 |

OTHER PUBLICATIONS

Fredrik Tinmark "Analysis of Elite Golfers' Kinematic Sequence in Full and Partial Shots" Sep. 23, 2008.

* cited by examiner

*Primary Examiner* — Edward Raymond
(74) *Attorney, Agent, or Firm* — Oliff PLC (57) ABSTRACT

A motion analysis method includes: specifying plural operations included in a motion operation using an output from an inertial sensor; calculating an operating time of each of the plural operations; adjusting a time axis of each operating time; and outputting operation information of the operation based on the adjusted time axis.

14 Claims, 6 Drawing Sheets

MOTION ANALYSIS METHOD AND MOTION ANALYSIS APPARATUS

CROSS REFERENCE

The entire disclosure of Japanese Patent Application No. 2013-213476 filed Oct. 11, 2013 is expressly incorporated by reference herein.

BACKGROUND

1. Technical Field

The present invention relates to a motion analysis method and a motion analysis apparatus.

2. Related Art

A motion analysis apparatus for golf, tennis, baseball or the like is used for analysis of a motion such as a swing operation. The motion analysis apparatus is configured such that an inertial sensor is attached to a swing device, a hand or an arm and respective operations of the swing operation are specified based on an output of the inertial sensor. For example, in the swing operation of a user, a state where a posture of a swing device that is swung is changed on a time axis is specified based on the output from the inertial sensor. When the respective operations are specified, the motion analysis apparatus guides a timing of the specified operation to the user. As a specific example of such a motion analysis apparatus, for example, a portable terminal device, a swing measurement method, and a measurement program disclosed in JP-A-2010-68947 are used.

Generally, a swing operation (motion) of hitting a ball in sports such as golf, tennis or baseball is approximately divided into two operations of an operation before hitting the ball, and an operation of hitting the ball and an operation after hitting the ball.

For example, a golf swing includes two operations of a back swing of swinging a golf club upward from a start position to a top position, which is an operation before hitting a ball; and a down swing of swinging the golf club down from the top position to hitting of the ball (impact), which is an operation of hitting the ball, and a follow-through from after the impact to a finish position, which is an operation after hitting the ball. In the golf swing, time necessary for the down swing and the follow-through is relatively shorter than time necessary for the back swing.

When such a swing operation is analyzed by the motion analysis apparatus and the analysis result is displayed on a time axis having the same unit width, it is difficult to understand the analysis result of the operation of hitting the ball and the operation after hitting the ball having the shorter time.

SUMMARY

An advantage of some aspects of the invention is to solve at least a part of the problems described above, and the invention can be implemented as the following forms or application examples.

APPLICATION EXAMPLE 1

This application example is directed to a motion analysis method including: calculating operating times of a first operation and a second operation in a motion using an output of an inertial sensor; adjusting a time axis of at least one of the first operation and the second operation; and outputting operation information of the first operation and the second operation.

According to such a motion analysis method, it is possible to obtain inertial data from the inertial sensor by moving a portion where the inertial sensor is attached. Plural operations are specified from the inertial data. Operating times of the specified plural operations are compared with each other. Then, for example, a time span (length of the time axis) of the longer operating time and a time span (length of the time axis) of the shorter operating time are adjusted to be approximately the same. By increasing the time span of the shorter operating time, it is possible to enhance readability in the motion analysis.

APPLICATION EXAMPLE 2

This application example is directed to the motion analysis method according to the application example described above, wherein the motion corresponds to a swing, the first operation corresponds to a back swing, and the second operation corresponds to a down swing.

APPLICATION EXAMPLE 3

This application example is directed to the motion analysis method according to the application example described above, wherein the motion analysis method further includes: detecting timings of a swing start, a top position, and impact in the swing using the output of the inertial sensor; and calculating the operating times of the first operation and the second operation based on the respective timings.

In such a motion analysis method, for example, in the golf swing, since the time of the down swing is shorter than the time of the back swing, by adjusting the time axis of the down swing to be lengthened, it is possible to easily view the output result.

APPLICATION EXAMPLE 4

This application example is directed to the motion analysis method according to the application example described above, wherein the output of the inertial sensor includes information about angular velocities generated around a plurality of axes, a timing of the impact is specified by a combined value of the angular velocities, and the timings of the top position and the start of the swing are specified based on the specified timing of the impact.

APPLICATION EXAMPLE 5

This application example is directed to the motion analysis method according to the application example described above, wherein a timing when the combined value of the angular velocities is the maximum is detected as the timing of the impact.

According to such a motion analysis method, it is possible to specify the plural operations in the swing from the combined value of the angular velocities. It is possible to specify each operation of the swing based on the impact timing obtained from the combined value of the angular velocities.

APPLICATION EXAMPLE 6

This application example is directed to the motion analysis method according to the application example described above, wherein the lengths of the time axes of the first operation and the second operation are adjusted to be the same.

According to such a motion analysis method, the motion is configured by plural operations including the first operation and the second operation. By adjusting the lengths of the time axes of the operating time of the first operation and the operating time of the second operation to be approximately the same, it is possible to enhance readability in comparison and analysis of the first operation and the second operation.

APPLICATION EXAMPLE 7

This application example is directed to the motion analysis method according to the application example described above, wherein the time axis of one operation of the first operation and the second operation is adjusted to be longer than the time axis of the other operation thereof.

APPLICATION EXAMPLE 8

In the motion analysis method according to this application example, the operation information of the first operation and the second operation may be displayed based on the adjusted time axis.

According to such a motion analysis method, for example, by adjusting a time span (length of the time axis) of an interest operation that is an operation to which an interest is directed, among the plural operations, to be longer than the time spans (lengths of the time axes) of the other operations for display, it is possible enhance readability in comparison and analysis of the interest operation and the other operations.

APPLICATION EXAMPLE 9

This application example is directed to a motion analysis apparatus including: an inertial sensor; a data obtaining section that obtains inertial data output from the inertial sensor; and an operation specifying section that specifies a plurality of operations of a motion based on the inertial data, in which the operation specifying section includes a time calculating section that calculates an operating time of the plurality of operations, a time axis adjusting section that adjusts a time axis of the operating time, and an operation information output section that outputs operation information of the plurality of operations based on the adjusted time axis.

According to such a motion analysis apparatus, the data obtaining section can obtain inertial data output from the inertial sensor in the plural operations by moving a portion where the inertial sensor is attached. The operation specifying section specifies the plural operations from the inertial data. The time calculating section calculates an operating time of each of the plural operations. The time axis adjusting section adjusts the time axis of the operating time of each of the plural operations. Thus, the motion operations are selected, and the time spans (lengths of the time axes) of the respective selected operations are adjusted to be approximately the same. The operation information output section outputs operation information for each of the plural operations based on the adjusted time axis. Thus, for example, a user can visually recognize the series of operations from the start of the swing to the finish of the swing, thereby making it possible to enhance readability.

BRIEF DESCRIPTION OF THE DRAWINGS

The invention will be described with reference to the accompanying drawings, wherein like numbers reference like elements.

DESCRIPTION OF EXEMPLARY EMBODIMENTS

As an embodiment of a motion analysis apparatus according to the invention, a motion analysis apparatus that performs analysis of a swing using a golf club will be described with reference to the accompanying drawings.

Here, a swing operation using the golf club will be briefly described.

First, the start of the swing refers to a state where a user holds the golf club to start the swing. A back swing refers to an operation of swinging up the head of the golf club from the start of the swing to the highest point. A top of the swing refers to the highest point when the head is swung up. A pause at the top position refers to a state where the head remains at the highest point. A down swing refers to an operation of swinging down the golf club from the top position to immediately before the impact. The impact refers to a state where the head hits a ball. A follow-through is an operation from the impact to the finish of the swing.

In the respective drawings described below, the size of each layer or each member is different from the actual size so that each layer or each member has a recognizable size. Further, embodiments are only examples, and thus, a configuration in which a part of components (respective units) is not provided or a configuration in which a component is added thereto may be used.

1. Configuration of Motion Analysis Apparatus

Figure 1:
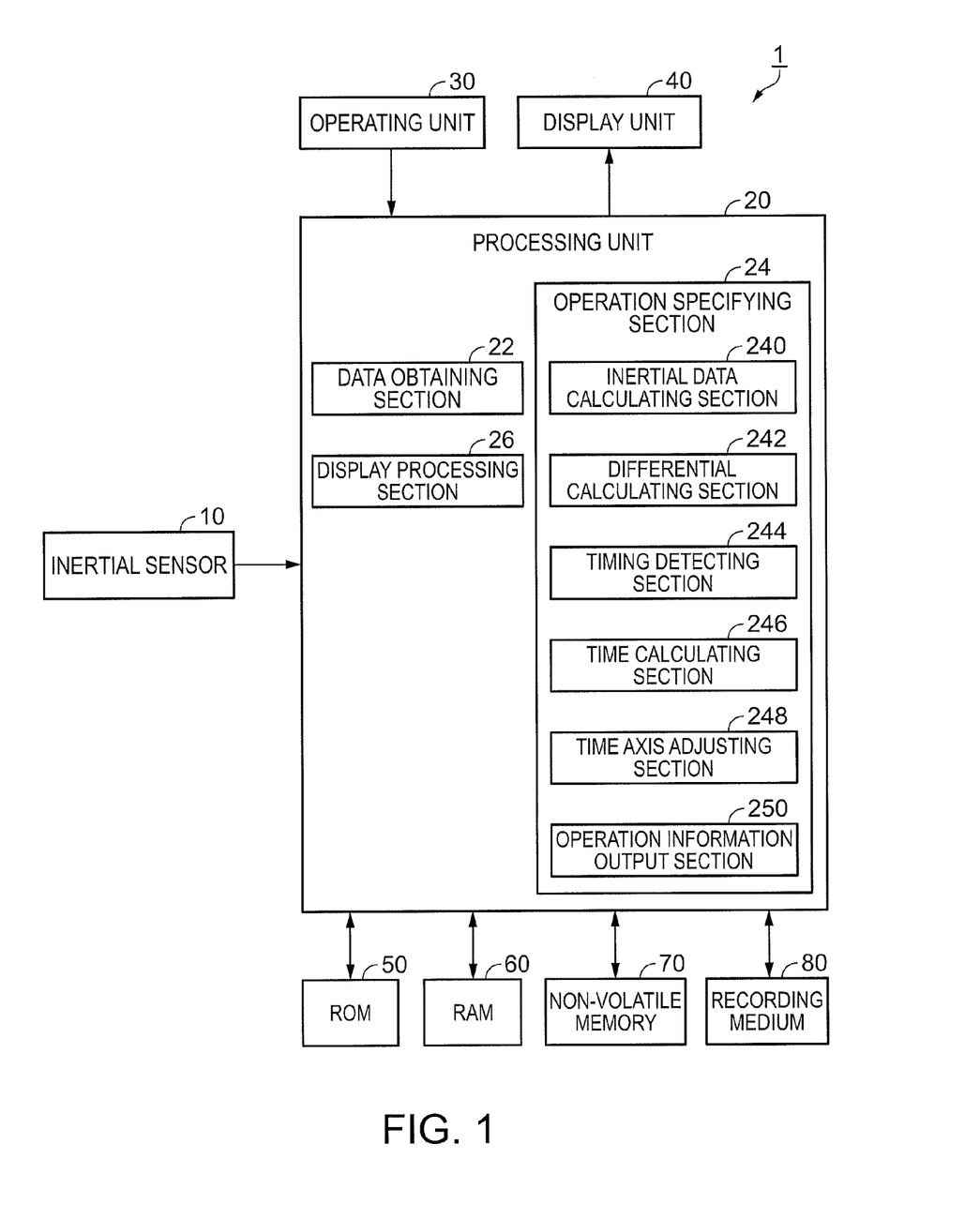
FIG. 1 is a diagram illustrating a configuration example of a motion analysis apparatus according to an embodiment of the invention.

FIG. 1 is a diagram illustrating a configuration example of the motion analysis apparatus according to the present embodiment. A configuration of a motion analysis apparatus 1 of the present embodiment will be described with reference to FIG. 1.

The motion analysis apparatus 1 of the present embodiment includes an inertial sensor 10, a processing unit 20, an operating unit 30, a display unit 40, a read only memory (ROM) 50, a random access memory (RAM) 60, a nonvolatile memory 70, and a recording medium 80.

In the present embodiment, an angular velocity sensor that detects an angular velocity is built into the inertial sensor 10. The angular velocity sensor detects angular velocities around plural axes generated according to a swing operation that is a motion operation, and outputs inertial data of the angular velocities around the respective axes. The angular velocity sensor may be a multiaxial sensor capable of detecting the angular velocities around the plural axes using one element, or may be a sensor mounted with plural uniaxial sensors capable of detecting the angular velocity around a single axis using one element.

The operating unit 30 obtains operation data input from a user, and transmits the operation data to the processing unit 20. The operating unit 30 may be a touch panel display, buttons, keys, a microphone or the like, for example.

The display unit 40 displays a processing result of the processing unit 20 as characters, graphs or other images. The display unit 40 is a cathode ray tube (CRT), a liquid crystal display (LCD), a touch panel display, a head mounted display (HMD) or the like, for example. The functions of the operating unit 30 and the display unit 40 may be realized by a touch panel display.

The ROM 50 stores a basic program, or data used in the basic program or the like for performing various calculation processes or control processes in the processing unit 20.

The RAM 60 is used as a work area of the processing unit 20, and temporarily stores a program or data read from the ROM 50 or the recording medium 80, data input from the operating unit 30, a calculation result executed according to the various programs by the processing unit 20, or the like.

The non-volatile memory 70 stores data necessary for long-term storage among data generated by the processing of the processing unit 20.

The recording medium 80 stores an application program or data for executing various application functions, and for example, may be realized by an optical disc (Compact Disc (CD), DVD, Blu-ray (registered trademark) Disc (BD)), a magneto-optical (MO) disc, a magnetic disc, a hard disk, a magnetic tape, a memory (ROM, flash memory or the like).

The processing unit 20 performs various processes (obtainment of inertial data of the inertial sensor 10, various calculations, various controls or the like) according to the basic program stored in the ROM 50 or the application program stored in the recording medium 80. The processing unit 20 may be realized by a microprocessor or the like.

Further, the processing unit 20 includes a data obtaining section 22, an operation specifying section 24, and a display processing section 26 to be described later, and analyzes respective operations of a swing operation of the user. The processing unit 20 executes a motion analysis program stored in the recording medium 80 to function as the data obtaining section 22, the operation specifying section 24, and the display processing section 26.

Alternatively, the motion analysis apparatus 1 may include a communicating unit to receive a motion analysis program from an external server through a wired or wireless communication network with the communicating unit, and the received motion analysis program may be stored in the RAM 60 or the recording medium 80 to execute the motion analysis program. Further, at least part of the data obtaining section 22, the operation specifying section 24, and the display processing section 26 may be realized by hardware (exclusive circuit).

The data obtaining section 22 obtains inertial data output from the inertial sensor 10 as the user performs the swing operation. The obtained inertial data is stored in the RAM 60, for example. The swing operation of the user includes plural operations, and includes at least three operations in the present embodiment.

The operation specifying section 24 specifies the plural operations from the inertial data obtained by the data obtaining section 22. The operation specifying section 24 of the present embodiment includes an inertial data calculating section 240, a differential calculating section 242, a timing detecting section 244, a time calculating section 246, a time axis adjusting section 248, and an operation information output section 250, to specify two operations from the swing operation.

The inertial data calculating section 240 calculates total sum data that is the sum of sizes of angular velocities of the plural axes based on the inertial data obtained by the data obtaining section 22.

The differential calculating section 242 differentiates the total sum data of the angular velocities calculated by the inertial data calculating section 240 by time.

The timing detecting section 244 calculates a timing of an impact in the swing operation using a combined value such as the total sum data of the angular velocities calculated by the inertial data calculating section 240. The timing detecting section 244 may detect a timing when the total sum data of the angular velocities is the maximum as the impact timing. Alternatively, the timing detecting section 244 may detect a preceding timing in a time sequence, among a timing when a differential value of the total sum data of the angular velocities calculated by the differential calculating section 242 is the maximum and a timing when the differential value is the minimum, as the impact timing.

The operation specifying section 24 may detect, in the inertial data obtained prior to the impact detected by the timing detecting section 244 in the time sequence, a timing when the total sum data of the angular velocities calculated by the inertial data calculating section 240 is smallest, as a swing top position timing.

Further, the operation specifying section 24 may specify, in the inertial data obtained prior to the impact in the time sequence, a continuous segment where the total sum data of the angular velocities is equal to or smaller than a first threshold value, as a top position segment (pause at the top position).

In addition, the operation specifying section 24 may detect, a timing when the total sum data of the angular velocities is equal to or smaller than a second threshold value, in the inertial data obtained prior to the top position in the time sequence, as a swing start timing.

Further, the operation specifying section 24 may detect, in the inertial data subsequent to the impact in the time sequence, the timing when the total sum data of the angular velocities is smallest, as a swing finish timing. Alternatively, the operation specifying section 24 may detect, in the inertial data subsequent to the impact in the time sequence, a first timing when the total sum data of the angular velocities is equal to or smaller than a third threshold value, as the swing finish timing.

In addition, the operation specifying section 24 may specify, in the inertial data subsequent to and close to the impact timing in the time sequence, a continuous segment where the total sum data of the angular velocities is equal to or smaller than a fourth threshold value, as a follow-through segment.

Thus, the operation specifying section 24 divides the swinging operation into respective operations of "start of the swing", "back swing", "top position of the swing", "pause at the top position", "down swing", "impact", "follow-through", and "finish of the swing".

Among the divided swing operations, an operation including the start of the swing, the back swing and the top position of the swing is referred to as a swing-up operation. Further, an operation including the pause at the top position, the down swing, the impact, the follow-through, and the finish of the swing may be referred to as a swing-down operation.

As described above, the operation specifying section 24 specifies the swing operation into the plural operations.

Further, at least one operation among the divided swing operations may be set as an interest operation to which a user's interest is directed.

The time calculating section 246 calculates times of the plural operations specified by the operation specifying section 24.

The time axis adjusting section 248 selects the swing-up operation that is the operation specified by the operation specifying section 24 as a first operation, and selects the swing-down operation as a second operation. Further, the lengths of the time of the first operation and the time of the second operation are compared with each other.

From the comparison result, the time span (length of the time axis) of the shorter operation is adjusted to be approximately the same as the time span (length of the time axis) of the longer operation. In the present embodiment, the time axis represents a time range of the first operation and the second operation.

Further, the time span (length of the time axis) of the interest operation may be adjusted to be longer than the time spans of the other operations.

In addition, the back swing may be selected as the first operation, and the down swing may be selected as the second operation.

The operation information output section 250 outputs operation information of the first operation and the second operation adjusted by the time axis adjusting section 248.

The display processing section 26 displays the operation information output from the operation information output section 250 on a screen (display unit 40).

The processing unit 20 of the present embodiment is only an example, and thus, a configuration in which a part of the components (respective sections) is not provided, or a configuration in which a component is added thereto may be used.

All or a part of the functions of the processing unit 20, the operating unit 30, the display unit 40, the ROM 50, the RAM 60, the non-volatile memory 70, and the recording medium 80 may be realized by a personal computer (PC), a mobile device such as a smart phone, or the like.

The motion analysis apparatus 1 may be configured as a separation type in which the inertial sensor 10 and the processing unit 20 are physically separated from each other, and in this case, data communication between the inertial sensor 10 and the processing unit 20 may be performed in a wireless or wired manner. Alternatively, the motion analysis apparatus 1 may be configured as an integrated type in which the inertial sensor 10 and the processing unit 20 are provided in a single case.

Figure 2A:
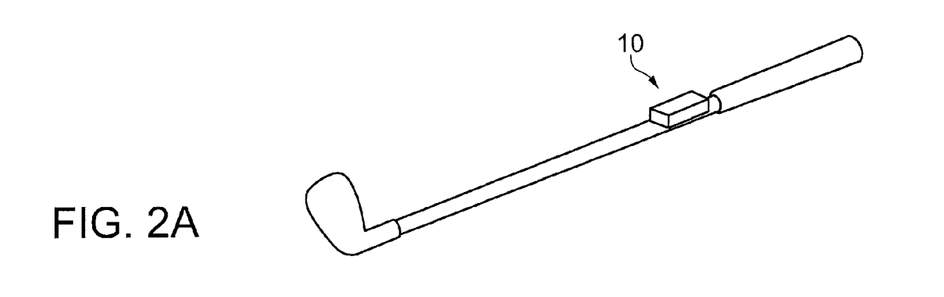
FIGS. 2A to 2C are diagrams illustrating an example of a mounting position of an inertial sensor.
Figure 2B:
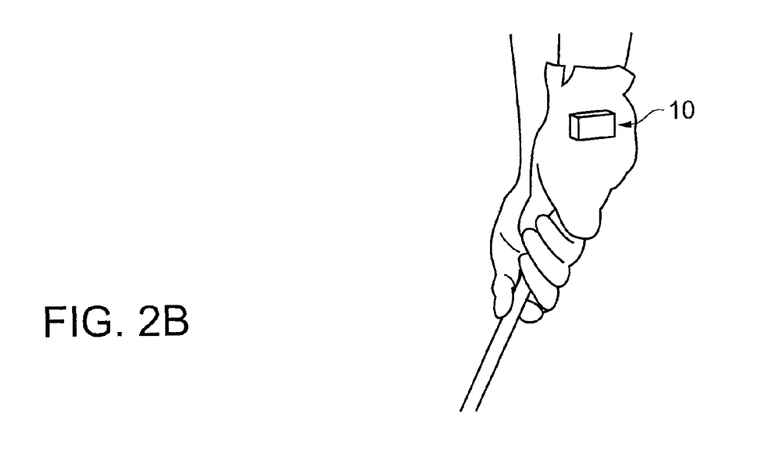
Figure 2C:
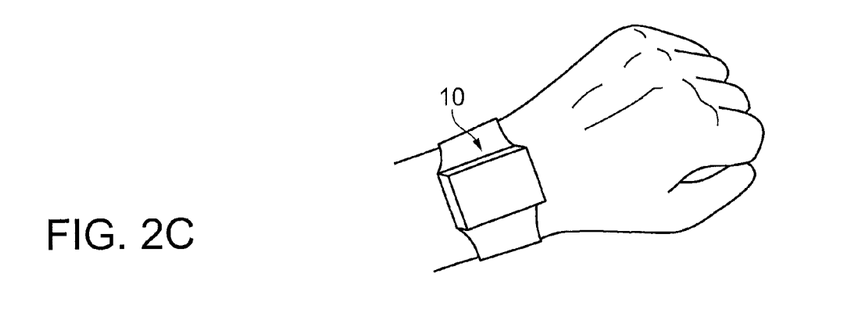

When the motion analysis apparatus 1 is configured as the separation type, the inertial sensor 10 may be attached at an arbitrary position where the angular velocities generated according to the swing operation can be detected. For example, the inertial sensor 10 is attached to an exercise device such as a golf club, as shown in FIG. 2A. Here, it is preferable that the inertial sensor 10 be attached to a shaft as shown in the figure, in order not to be affected by a shock on impact. In addition, the inertial sensor 10 may be attached to the body of the user, a glove or the like as shown in FIG. 2B, or may be attached to a watch, an accessory or the like as shown in FIG. 2C.

Further, when the motion analysis apparatus 1 is configured as the integrated type, the motion analysis apparatus 1 may be attached to an exercise device such as a golf club, the user's body, clothing, a protector, an accessory or the like.

2. Process of Motion Analysis Apparatus
2-1. Entire Process of Motion Analysis

Figure 3:
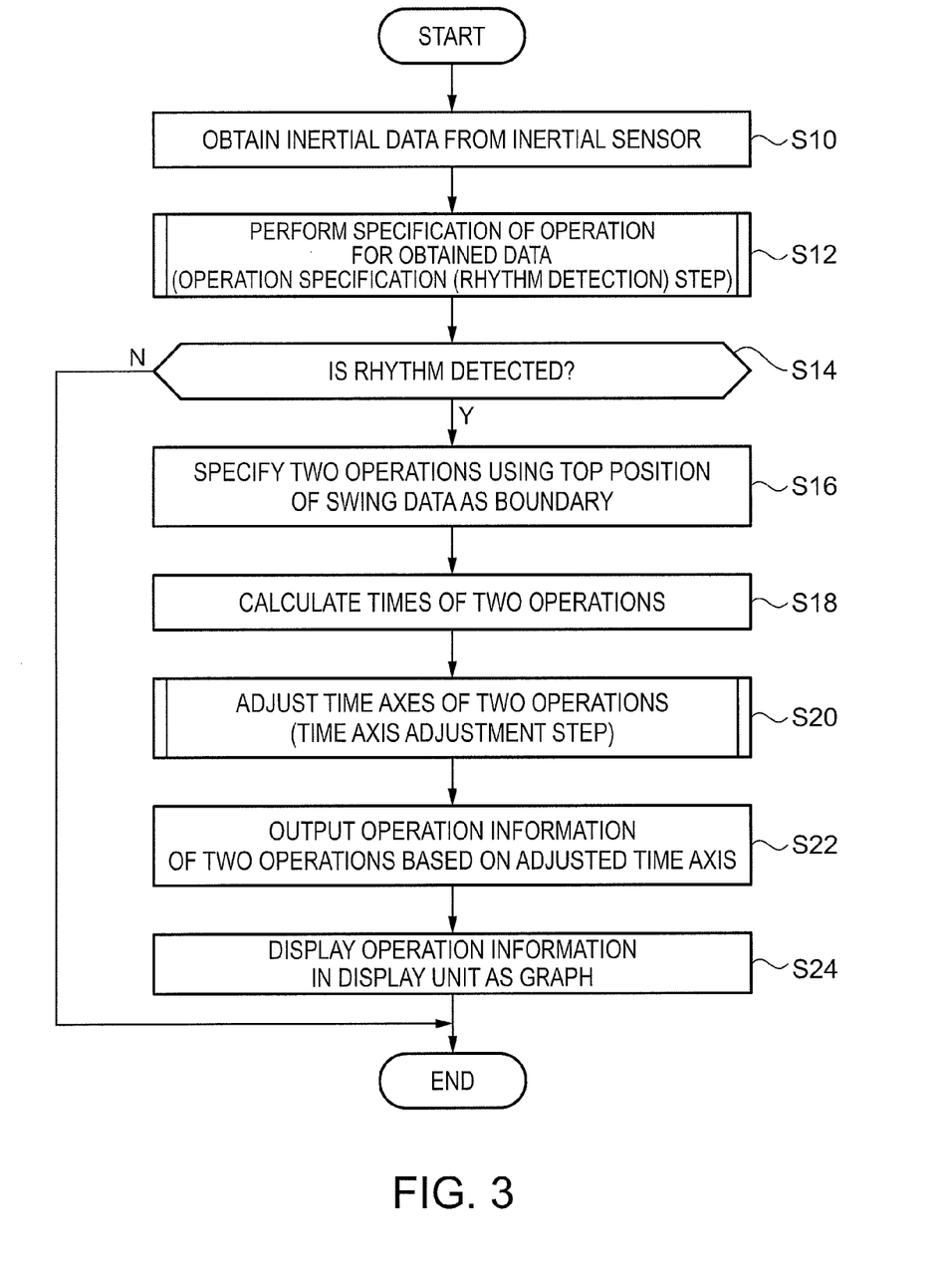
FIG. 3 is a flowchart illustrating an example of the entire process of a motion analysis.

FIG. 3 is a flowchart illustrating an example of the entire process of a motion analysis in the processing unit 20 of the motion analysis apparatus 1. Hereinafter, the description of FIG. 3 will be made with reference to FIG. 1.

In the description, the terms of "before", "after", "preceding" represent positions in the time sequence.

As shown in FIG. 3, the processing unit 20 of the present embodiment functions as the data obtaining section 22 to obtain the inertial data from the inertial sensor 10 (step S10).

A period (data obtaining period) when the data obtaining section 22 obtains the inertial data from the inertial sensor 10 is set by an arbitrary method. For example, a user or an assistant may operate the operating unit 30 before the start of the swing to indicate a start timing of the data obtaining period, and may operate the operating unit 30 after the finish of the swing to indicate a finish timing of the data obtaining period. Further, for example, the user or the assistant may operate the operating unit 30 before the start of the swing to indicate the start timing of the data obtaining period, and the data obtaining period may automatically finish after a predetermined time elapses.

Then, the processing unit 20 functions as the operation specifying section 24 to perform an operation specification (rhythm detection) for the inertial data obtained in step S10 (step S12, operation specification step). Here, "rhythm" represents a rhythm of the series of operations from the start of the swing to the finish of the swing. For example, in the case of the golf swing, the rhythm corresponds to the start of the swing, the back swing, the top position, the pause at the top position, the down swing, the impact, the follow-through, and the finish of the swing.

When the rhythm detection is not performed from the operation specified in step S12 (N in step S14), it is determined that data (swing data) corresponding to the swing operation is not included in the obtained inertial data, and then the process is finished. In this case, information indicating that the swing data is not included in the obtained inertial data may be displayed in the display unit 40.

On the other hand, when the rhythm detection is performed from the operation specified in step S12 (Y in step S14), the processing unit 20 functions as the operation specifying section 24 to specify two operations of the swing-up operation and the swing-down operation using the top position of the swing data as a boundary (step S16).

Then, the time calculating section 246 of the operation specifying section 24 calculates the time of the swing-up operation (top position time T3−swing start time T1) and the time of the swing-down operation (swing finish time T8−top position time T3) from the two operations specified in step S16 (step S18).

The times necessary for the operations are represented as the swing start time T1, a top position segment start time T2, the top position time T3, a top position segment finish time T4, an impact time T5, a follow-through segment start time T6, a follow-through segment finish time T7, and the finish time T8.

Then, the time axis adjusting section 248 of the operation specifying section 24 performs adjustment so that the lengths of the time axes of the two operations are approximately equal to each other based on the times of the two operations specified in step S16 and step S18 (step S20, time axis adjustment step).

Then, the operation information output section 250 of the operation specifying section 24 outputs operation information the time axes of which are adjusted in step S20 are adjusted (step S22).

Then, the processing unit 20 functions as the display processing section 26 to display the operation information output in step S22, that is, the swing data in which the time axes of two operations corresponding to the swing operation of the user are adjusted, as a graph in the display unit 40 (step S24), and then finishes the process.

2-2. Operation Specification (Rhythm Detection) Process

Figure 4:
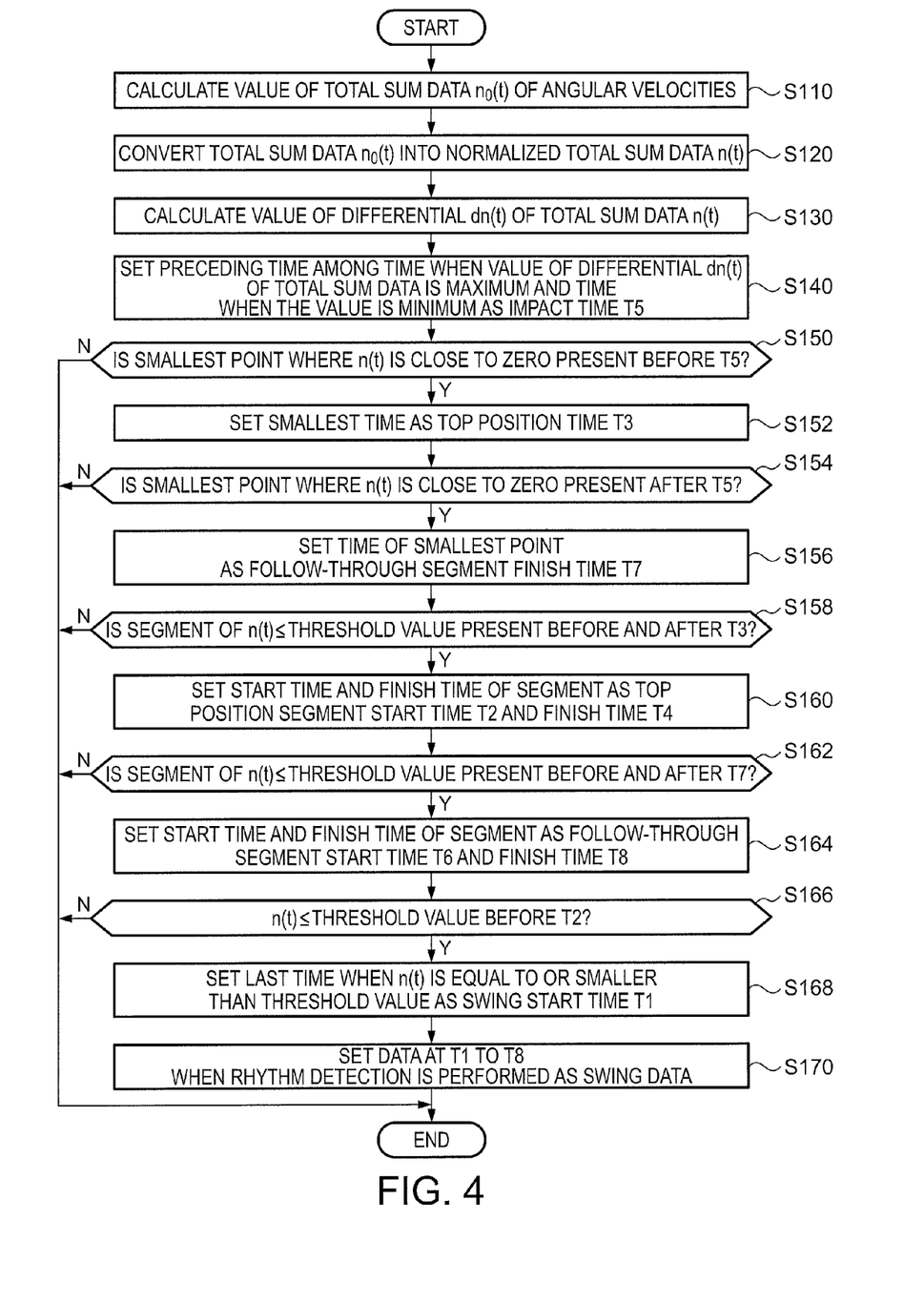
FIG. 4 is a flowchart illustrating an example of an operation specification (rhythm detection) process.

FIG. 4 is a flowchart illustrating an example of an operation specification (rhythm detection) process using the processing unit 20 (operation specifying section 24). Hereinafter, the description of FIG. 4 will be made with reference to FIG. 1.

As shown in FIG. 4, the processing unit 20 (operation specifying section 24) functions as the inertial data calculating section 240 to calculate a value of total sum data $n_0(t)$ that is a combined value of angular velocities at each time t from the obtained data (step S110).

As an example of a method of calculating the combined value of the angular velocities (the sum of the sizes of the angular velocities), there is a method of calculating the combined value from the "square root of the sum of squares of the sizes of the angular velocities". Here, the inertial sensor 10 detects the angular velocity around three axes, and when detection data corresponding to three axes at each time t during the data obtaining period is represented as x(t), y(t), and z(t), the total sum data $n_0(t)$ of the angular velocities is calculated by the following expression (1).

$$n_0(t) = \sqrt{x(t)^2 + y(t)^2 + z(t)^2} \quad (1)$$

Then, the processing unit 20 (operation specification section 24) converts the total sum data $n_0(t)$ of the angular velocities at each time t into total sum data n(t) normalized in a predetermined range (step S120). Specifically, when the maximum value of the total sum data of the angular velocities in the data obtaining period is represented as max $(n_0)$, the total sum data $n_0(t)$ of the angular velocities is converted into the total sum data n(t) that is normalized in the range of 0 to 100, by the following expression (2).

$$n(t) = \frac{100 \times n_0(t)}{\max(n_0)} \quad (2)$$

Then, the processing unit 20 (operation specification section 24) functions as the differential calculating section 242 to calculate a value of a differential dn(t) of the total sum data (normalized total sum data) n(t) at each time t (step S130). For example, when an obtainment interval of the detection data of the angular velocities is represented as Δt, the differential (difference) dn(t) of the total sum data of the angular velocities at time t is calculated by the following expression (3).

$$dn(t) = n(t) - n(t - \Delta t) \quad (3)$$

Then, the processing unit 20 (operation specifying section 24) functions as the timing detecting section 244 to set, among the time when the value of the differential dn(t) of the total sum data is the maximum and the time when the value is the minimum, the preceding time as the impact time T5 (step S140).

In a normal golf swing, it is considered that the swing speed is the maximum at the moment of impact. Further, since it is considered that the value of the total sum data of the angular velocities is also changed according to the swing speed, it is possible to handle a timing when the differential value of the total sum data of the angular velocities is the maximum or the minimum (that is, a timing when the differential value of the total sum data of the angular velocities is a positive maximum value or a negative minimum value) in the series of swing operation as the impact timing. Since the golf club vibrates due to the impact, it is considered that a pair of timings, that is, the timing when the differential value of the total sum data of the angular velocities is the maximum and the timing when the differential value is the minimum are generated, but the preceding timing is considered as the impact moment.

Then, the processing unit 20 (operation specifying section 24 determines whether the smallest point where the value of the total sum data n(t) that is normalized before the impact time T5 is close to zero is present (step S150), and if the smallest point is present (Y in step S150), the processing unit 20 sets the time of the smallest point as the top position time T3 (step S152). In the normal golf swing, it is considered that after the start of the swing, the operation is stopped once at the top position, and then, the swing speed gradually increases to reach the impact. Accordingly, it is possible to handle a timing when the total sum data of the angular velocities is close to zero and is smallest before the impact timing as the top position timing.

On the other hand, if the smallest point where the value of the total sum data n(t) is close to zero is not present before the impact time T5 (N in step S150), the processing unit 20 (operation specifying section 24) determines that the rhythm detection for the obtained data fails (swing data is not included in the obtained data), and finishes the process.

Then, the processing unit 20 (operation specifying section 24) determines whether the smallest point where the value of the total sum data n(t) is close to zero is present after the impact time T5 (step S154), and if the smallest point is present (Y in step S154), the processing unit 20 sets the time at the smallest point as the follow-through segment finish time T7 (step S156). In the normal golf swing, it is considered that after the impact, the swing speed gradually decreases to be stopped. Accordingly, it is possible to handle a timing when the total sum data of the angular velocities is close to zero and is smallest after the impact timing as the follow-through timing.

On the other hand, if the smallest point where the value of the total sum data n(t) is close to zero is not present after the impact time T5 (N in step S154), the processing unit 20 (operation specifying section 24) determines that the rhythm detection for the obtained data fails (swing data is not included in the obtained data), and finishes the process.

Then, the processing unit 20 (operation specifying section 24) determines whether a segment where the value of the total sum data n(t) is equal to or smaller than a predetermined threshold value (example of a first threshold value) is present before and after the top position time T3 (step S158), and if the segment is present (Y in step S158), the processing unit 20 sets a start time and a finish time of the segment as the top position segment start time T2 and the top position segment finish time T4, respectively (step S160). In the normal golf swing, since the operation is stopped once at the top position, it is considered that the swing speed is low before and after the top position. Accordingly, it is possible to handle a continuous segment where the top position timing is included and the total sum data of the angular velocities is equal to or smaller than the predetermined threshold value as the top position segment.

On the other hand, if the segment where the value of the total sum data n(t) is equal to or smaller than the threshold value is not present before and after the top position time T3 (N in step S158), the processing unit 20 (operation specifying section 24) determines that the rhythm detection for the obtained data fails (swing data is not included in the obtained data), and finishes the process.

Then, the processing unit 20 (operation specifying section 24) determines whether a segment where the value of the total sum data n(t) is equal to or smaller than a predetermined threshold value (example of a fourth threshold value) is present before and after the follow-through segment finish time T7 (step S162), and if the segment is present (Y in step S162), the processing unit 20 sets a start time and a finish time of the segment as the follow-through segment start time T6 and the finish time T8, respectively (step S164). In a normal golf swing, it is considered that the swing speed gradually decreases to be stopped after the impact. Accordingly, it is possible to handle a continuous segment where the follow-through timing is included and the total sum data of the angular velocities is equal to or smaller than the predetermined threshold value as the follow-through segment.

On the other hand, if the segment where the value of the total sum data n(t) is equal to or smaller than the threshold value is not present before and after the follow-through segment finish time T7 (N in step S162), the processing unit 20 (operation specifying section 24) determines that the rhythm detection for the obtained data fails (swing data is not included in the obtained data), and finishes the process.

Then, the processing unit 20 (operation specifying section 24) determines whether the value of the total sum data n(t) is equal to or smaller than a predetermined threshold value (example of a second threshold value) is present before the top position segment start time T2 (step S166), and if the value is equal to or smaller than the threshold value (Y in step S166), the processing unit 20 sets the last time when the value is equal to or smaller than the threshold value as the swing start time T1 (step S168). Before the smallest point where the top position is specified, the smallest point where the total sum data is close to zero may be considered as the swing start point. In a normal golf swing, it is hardly considered that the swing operation is stopped between the start from the stationary state and the top position. Accordingly, it is possible to handle the last timing when the total sum data of the angular velocities is equal to or smaller than the threshold value before the top position timing as the start timing of the swing operation.

On the other hand, if the value of the total sum data n(t) is not equal to or smaller than the threshold value before the top position segment start time T2 (N in step S166), the processing unit 20 (operation specifying section 24) determines that the rhythm detection for the obtained data fails (swing data is not included in the obtained data), and finishes the process.

Finally, the processing unit 20 (operation specifying section 24) sets the data at times T1 to T8 when the rhythm detection is performed as swing data (step S170), and finishes the process.

The respective threshold values of the top position segment, the follow-through segment, and the swing start are stored in the ROM 50, the RAM 60 or the like as table data, for example. These threshold values may be fixed values, or maybe variable values (for example, set individually for each user). If the respective threshold values are provided corresponding to the respective operations, even when plural smallest points occur, it is possible to easily extract the smallest points corresponding to the swing.

The respective steps of the flowchart of FIG. 4 may be appropriately exchanged.

Further, in the flowchart of FIG. 4, the process of calculating the value of the differential dn(t) of the total sum data (normalized total sum data) n(t) at each time t (step S130) maybe omitted. Particularly, in a case where the change of the total sum data of the angular velocities is large as in a driver swing of the golf club, the differentiation process (step S130) may be omitted. When step S130 is omitted, the maximum value of the total sum data of the angular velocities obtained in step S120 may be detected as the impact timing.

Further, in steps S154 and S156 of the flowchart of FIG. 4, the smallest point where the value of the total sum data n(t) of the angular velocities is close to zero after the impact timing is represented as the follow-through timing, but for example, the first timing when the value of the total sum data n(t) of the angular velocities is equal to or smaller than a predetermined value (example of a third threshold value) after the impact may be set as the follow-through timing of the swing.

2-3. Time Axis Adjustment Process

Figure 5:
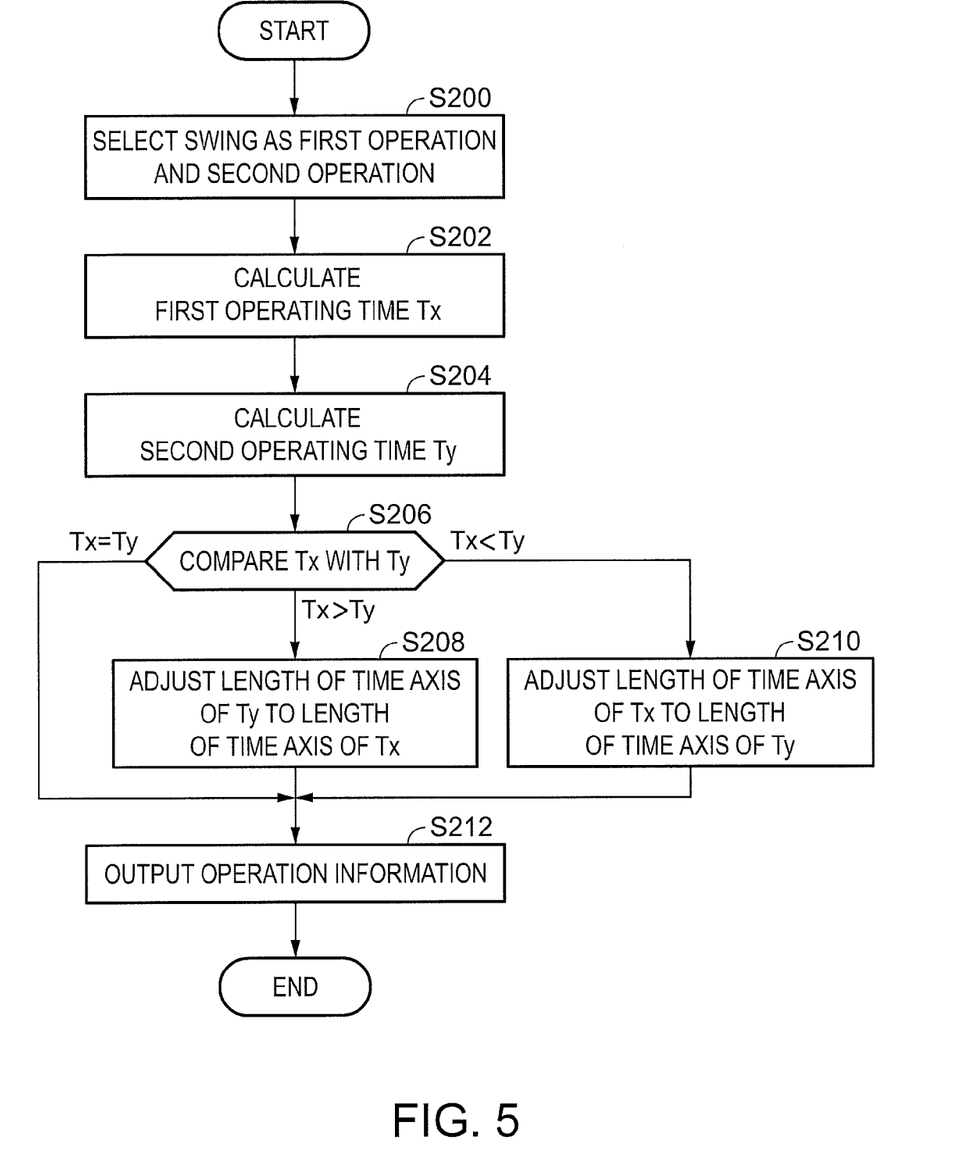
FIG. 5 is a flowchart illustrating an example of a time axis adjustment process.

FIG. 5 is a flowchart illustrating an example of a time axis adjustment process using the processing unit 20 (time axis adjusting section 248). Hereinafter, the time axis adjustment process will be described with reference to FIGS. 1 and 5.

As shown in FIG. 5, the processing unit 20 (operation specifying section 24) of the present embodiment first functions as the time axis adjusting section 248 to select the swing-up operation (the swing start time T1 to the top position time T3) as a first operation and the swing-down operation (the top position time T3 to the finish time T8) as a second operation based on the swing data obtained in the operation specifying (rhythm detection) step using the swing top position as a boundary (step S200).

Then, the processing unit 20 (time axis adjusting section 248) calculates a time of the first operation selected in step S200 as (Tx=top position time T3−swing start time T1) (S202).

Then, the processing unit 20 (time axis adjusting section 248) calculates a time of the second operation selected in step S200 as (Ty=finish time T8−top position time T3) (S204).

Then, the processing unit 20 (time axis adjusting section 248) compares the first operating time Tx with the second operating time Ty (step S206).

When the first operating time Tx is larger than the second operating time Ty (Tx>Ty in step S206), the length of the time axis (graph range) of the second operating time Ty is adjusted to be approximately the same as the length of the time axis of the first operating time Tx. That is, the length of the time axis of the second operating time Ty is multiplied by (Tx/Ty) (step S208). Then, the procedure proceeds to step S212.

Further, when the first operating time Tx is smaller than the second operating time Ty (Tx<Ty in step S206), the length of the time axis (graph range) of the first operating time Tx is adjusted to be approximately the same as the length of the time axis of the second operating time Ty. That is, the length of the time axis of the first operating time Tx is multiplied by (Ty/Tx) (step S210). Then, the procedure proceeds to step S212.

Further, when the first operating time Tx is the same as the second operating time Ty (Tx=Ty in step S206), the procedure proceeds to step S212.

Then, the processing unit 20 (time axis adjusting section 248) outputs operation information of the respective operations to the operation information output section 250 based on the time axis adjusted in step S208 and step S210 (S212), and then finishes the process. In the present embodiment, when the time difference does not occur at Tx and Ty, the length of the time axis is not adjusted.

2-4. Motion Analysis Display Process

Figure 6:
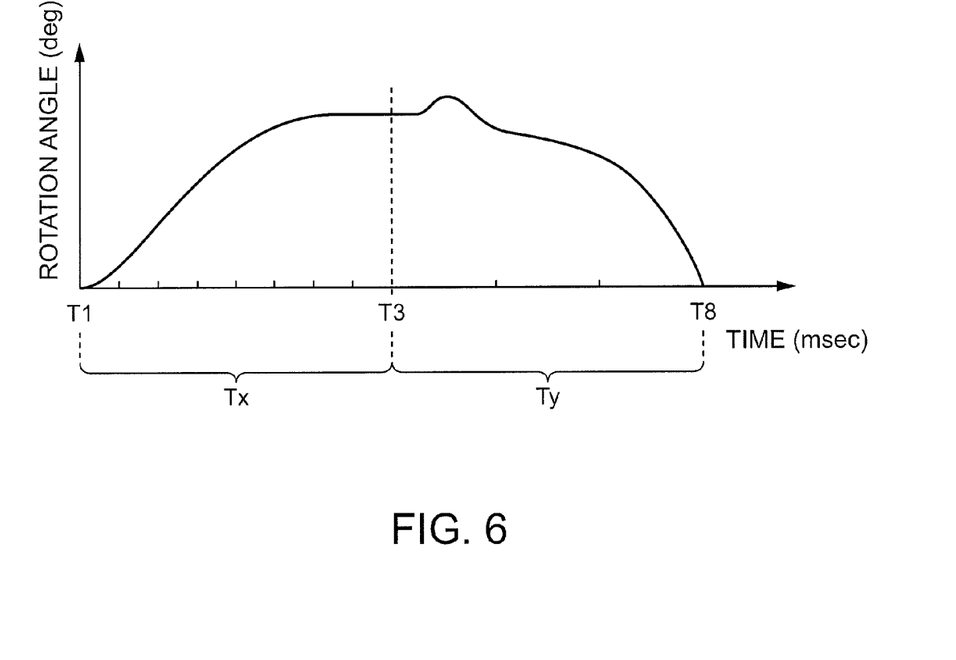
FIG. 6 is a diagram illustrating an example of display of a motion analysis using a motion analysis apparatus.

FIG. 6 is a diagram illustrating an example of display of a motion analysis of a golf swing using the processing unit 20 (display processing section 26). Hereinafter, the motion analysis display will be described with reference to FIGS. 1 and 6.

FIG. 6 is a graph illustrating the swing start time T1, the first operating time Tx, the swing top position time T3, the second operating time Ty, and the finish time T8 displayed in the display processing section 26 in the time sequence based on the operation information output by the operation information output section 250. The lengths of the time axes of the first operating time Tx and the second operating time Ty are equalized.

The display processing unit 26 integrates the angular velocities of the respective operations included in the operation information, calculates a rotation angle of the swing, and displays the result in the display unit 40 as a graph. In the graph of FIG. 6, the transverse axis represents time (msec), and the longitudinal axis represents the rotation angle (deg).

In the figure, numerical values of scales of both axes, the top position segment start time T2, the top position segment finish time T4, the impact time T5, the follow-through segment start time T6, and the follow-through segment finish time T7 are not shown. Hereinafter, the equalization of the lengths of the time axes will be described.

In FIG. 6, the first operating time Tx includes eight areas on the time axis, and the second operating time Ty has three areas on the time axis.

In the present embodiment, since the first operating time Tx is larger than the second operating time Ty, the length of the time axis of the second operating time Ty is multiplied by (Tx/Ty). Specifically, the second operating time Ty is multiplied by (8/3). Thus, the second operating time Ty and the first operating time Tx can be set to have approximately the same length of the time axis.

Thus, it is possible to display the motion analysis in a state where the time axis of the first operation (swing-up operation) and the time axis of the second operation (swing-down operation) are the same.

Since it can be confirmed that the time of the swing-down operation becomes long, it is possible to obtain detailed information relating to the rhythm of the swing operation. Further, the entire swing rhythm may not only be displayed, and instead, the time may be also displayed for each swing operation.

As described above, according to the motion analysis apparatus 1 according to the present embodiment, the following effects can be obtained.

According to the present embodiment, by using the motion analysis apparatus 1, it is possible to display swing operations having different times in time sequence data in a golf swing to have approximately the same lengths of the time axes. Accordingly, it is possible to enhance readability in comparison and analysis of two operations (swing-up operation (back swing) and swing-down operation (down swing and follow-through)).

Further, according to the present embodiment, since the swing operation is detected based on the total sum data of the angular velocities, it is possible to attach the inertial sensor 10 in an arbitrary direction at a location that moves in association with the swing operation, which provides easy handling.

Further, according to the present embodiment, since the times of the respective operations in the swing operation are displayed, the user can easily recognize detailed rhythm of the swing operation.

In the present embodiment, the motion analysis apparatus that performs the swing analysis using the golf club is described, but the motion analysis apparatus according to the invention can enhance readability in analysis of a motion operation using various exercise devices such as a tennis racket or a baseball bat, or a motion operation such as an athletic sport including running long jump or hammer throw is analyzed.

What is claimed is:

1. A motion analysis method comprising:
obtaining data from an inertial sensor that is attached to an object held or worn by a user;
calculating operating times of a first operation and a second operation in a motion of the user or the object, based on the data from the inertial sensor;
adjusting a time axis of at least one of the first operation and the second operation to an adjusted time axis so that the first operation and the second operartion are on different time scales, based on the operating times;
applying the adjusted time axis to operation information of the first operation and the second operation; and
displaying, on a display, the operation information applied with the adjusted time axis.

2. The motion analysis method according to claim 1, wherein the motion corresponds to a swing, and
wherein the first operation corresponds to a back swing, and the second operation corresponds to a down swing.

3. The motion analysis method according to claim 2, further comprising:
detecting timings of a swing start, a top position, and an impact in the swing using the output of the inertial sensor; and
calculating the operating times of the first operation and the second operation based on the respective timings.

4. The motion analysis method according to claim 3, wherein the output of the inertial sensor includes information about angular velocities generated around a plurality of axes,
wherein a timing of the impact is specified by a combined value of the angular velocities, and
wherein the timings of the top position and the swing start are specified based on the specified timing of the impact.

5. The motion analysis method according to claim 4, wherein a timing when the combined value of the angular velocities is a maximum is detected as the timing of the impact.

6. The motion analysis method according to claim 1, wherein lengths of the time axes of the first operation and the second operation are adjusted to be the same.

7. The motion analysis method according to claim 1, wherein the time axis of one operation of the first operation and the second operation is adjusted to be longer than the time axis of an other operation of the first operation and the second operation.

8. The motion analysis method according to claim 1, wherein the operation information of the first operation and the second operation is displayed based on an adjusted time axis.

9. A motion analysis apparatus comprising:
an inertial sensor that is attached to an object held or worn by a user;

a data obtaining section that obtains inertial data output from the inertial sensor;

and an operation specifying section that specifies a plurality of operations of a motion of the user or the object, based on the data from the inertial data, the operation specifying section including:

a time calculating section that calculates operating times of the plurality of operations, a time axis adjusting section that adjusts a time axis of the operating time of at least one of the plurality of operations to an adjusted time axis so that at least one operation of the plurality of operations and the other operation or operations of the plurality of operations are on different time scales, and an operation information output section that applies the adjusted time axis to operation information of the plurality of operations, and displays, on a display, the operation information applied with the adjusted time axis.

10. A motion analysis method comprising:

obtaining data from an inertial sensor that is attached to an object held or worn by a user;

obtaining a plurality of operations in a motion of the user or the object, based on the data from the inertial sensor;

determining whether the plurality of operations satisfy a plurality of predetermined motion conditions;

dividing, responsive to a determination that the plurality of operations satisfy the plurality of predetermined motion conditions, the plurality of operations into a first operation and a second operation;

calculating operating times of the first operation and the second operation;

adjusting a time axis length of the operating time of one of the first operation and the second operation to an adjusted time axis, so that the first operation and the second operation are on different time scales, based on a time axis length of the operating time of another of the first operation and the second operation;

applying the adjusted time axis to operation information of the first operation and the second operation, the operation information including the operating times of the first operation and the second operation; and displaying, on a display, the operation information applied with the adjusted time axis.

11. The motion analysis method according to claim 10, wherein lengths of the time axes of the first operation and the second operation are adjusted to be the same.

12. The motion analysis method according to claim 10, wherein the plurality of operations are divided into the first operation and second operation according to a timing of a minimum output value of the inertial sensor occurring before a maximum output value of the inertial sensor.

13. The motion analysis method according to claim 10, wherein one of the predetermined motion conditions is whether, after a start of the motion, there is a relative minimum output value of the inertial sensor that is close to zero before a maximum output value of the sensor.

14. The motion analysis method according to claim 10, wherein one of the predetermined motion conditions is whether, before an end of the motion, there is a relative minimum output value of the inertial sensor that is close to zero after a maximum output value of the sensor.

* * * * *